United States Patent
Schroeder

(10) Patent No.: US 6,464,103 B1
(45) Date of Patent: Oct. 15, 2002

(54) DENTAL CLOTH

(76) Inventor: Deborah K. Schroeder, 60658 Walters Rd., Jacobsburg, OH (US) 43933

( * ) Notice: Subject to any disclaimer, the term of this patent is extended or adjusted under 35 U.S.C. 154(b) by 0 days.

(21) Appl. No.: 09/853,364

(22) Filed: May 10, 2001

(51) Int. Cl.[7] .................................................. B65H 1/00
(52) U.S. Cl. ........................ 221/47; 221/63; 206/63.5; 132/321; 433/216
(58) Field of Search ......................... 221/63, 47, 48; 433/216; 132/321, 323; 206/63.5, 233

(56) References Cited

U.S. PATENT DOCUMENTS

| | | | |
|---|---|---|---|
| 3,124,824 A | | 3/1964 | Lutz |
| 3,902,509 A | * | 9/1975 | Tundermann et al. |
| 3,913,596 A | * | 10/1975 | Stuart |
| 3,934,299 A | | 1/1976 | Regester |
| 4,335,731 A | * | 6/1982 | Bora, Jr. |
| D287,195 S | | 12/1986 | Billgren |
| 4,875,247 A | | 10/1989 | Berg |
| 4,972,946 A | * | 11/1990 | Whittaker ............... 132/324 X |
| 5,445,825 A | * | 8/1995 | Copelan et al. ............. 424/448 |
| 5,487,201 A | | 1/1996 | Hansen et al. |
| 5,518,012 A | * | 5/1996 | Dolan et al. ................ 132/321 |
| 5,560,379 A | * | 10/1996 | Pieczenik ................... 132/329 |
| 5,765,576 A | * | 6/1998 | Dolan et al. ................ 132/321 |
| 6,378,698 B1 | * | 4/2002 | Scoggins ............... 206/63.5 X |

FOREIGN PATENT DOCUMENTS

WO    WO95/31154    11/1995

* cited by examiner

Primary Examiner—David H. Bollinger
(74) Attorney, Agent, or Firm—Gene Scott-Patent Law & Venture Group

(57) ABSTRACT

A dental wiper provides a package having a front panel, a rear panel and a circumferential side panel joining the front and rear panels as an integral unit defining an interior space. The front panel provides an open slot extending substantially across the package. The open slot has a central access portion with clearance for finger tip entry into the interior space of the package. A plurality of dental sheets are arranged in a stack within the package. The dental sheets each have a width approximately equal to the slot width where the dental sheets position one edge of the sheets, adjacent to the access portion of the slot for being manually engaged for withdrawal. The sheets are useful for cleaning the surfaces of the teeth.

5 Claims, 2 Drawing Sheets

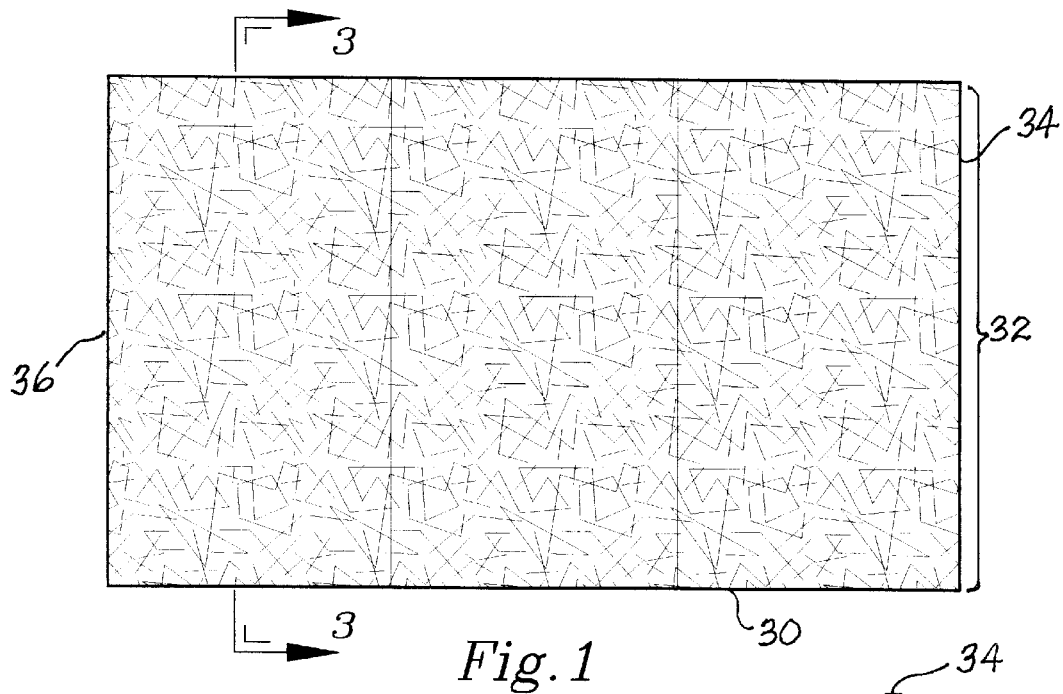
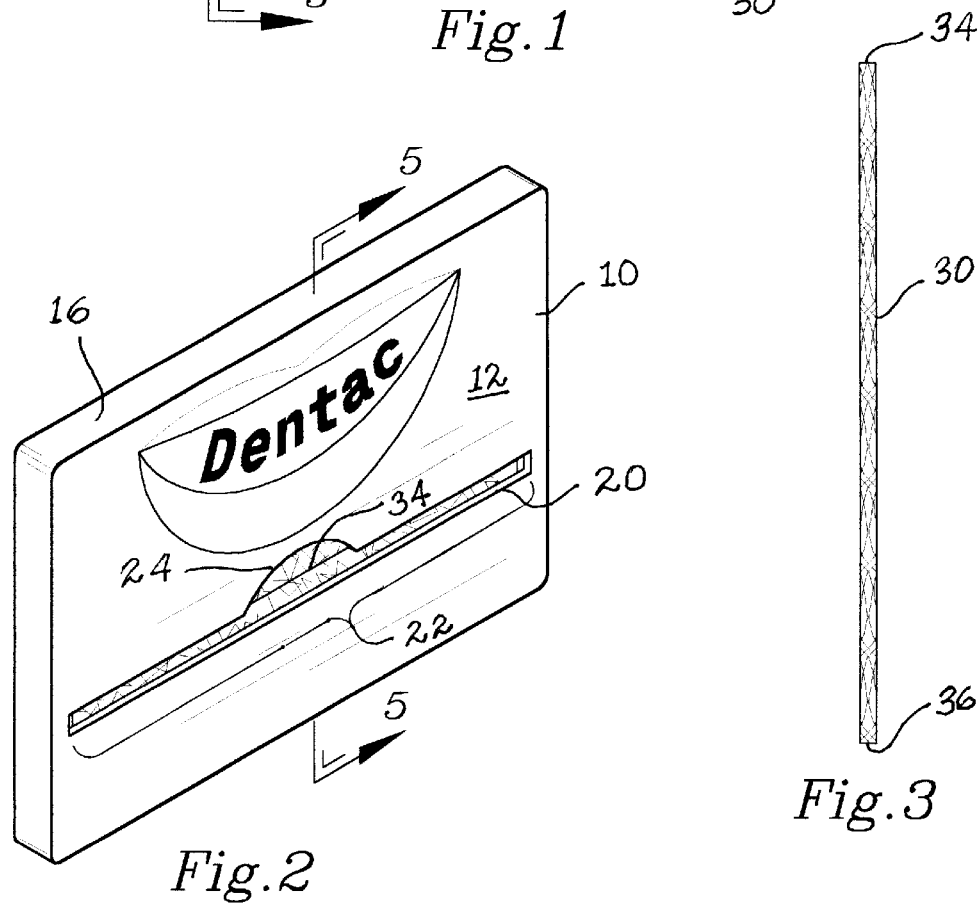

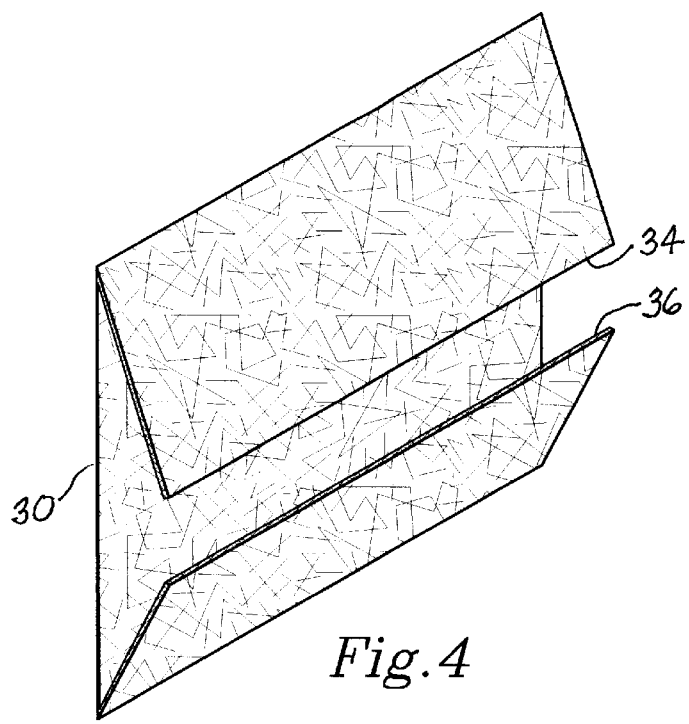
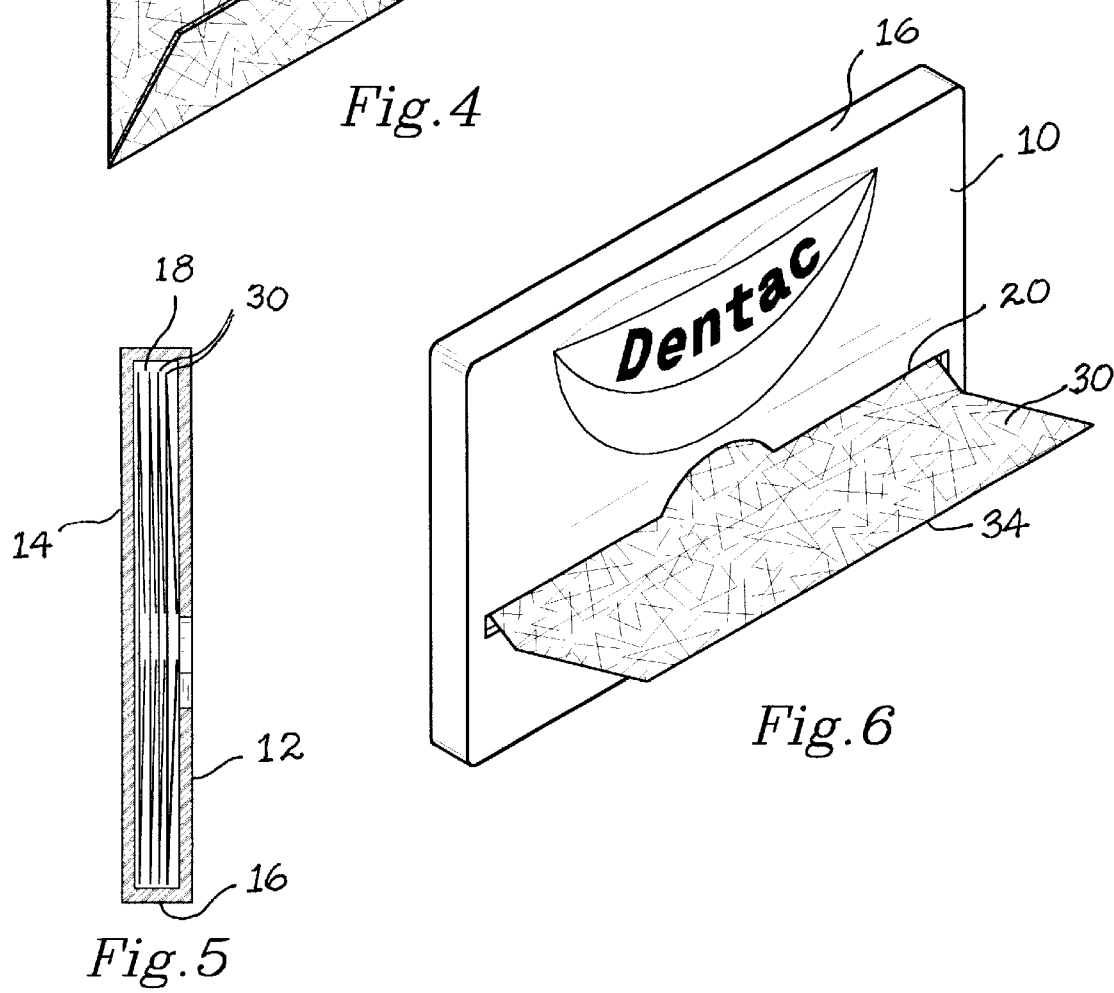

DENTAL CLOTH

BACKGROUND OF THE INVENTION

1. Field of the Invention

This invention relates generally to products for oral hygiene and especially products for cleaning the teeth and more particularly to a combination dental cloth and dispensing package.

2. Description of Related Art

The following art defines the present state of this field:

Billgren, U.S. Pat. No. D287,197 provides the ornamental design for an embossed cloth.

Lutz, U.S. Pat. No. 3,124,824 describes a tooth cleaning instrumentality formed of two layers of thin plastic film heat sealed along their longitudinal edges to form a cot, one layer being substantially longer than the other so as to project at the bottom of the cot to form a tab which may be grasped by the fingers of one hand for pulling the cot onto a finger of the other hand, the shorter layer of film having secured thereto a layer of plastic foam of substantially the same shape as said film layer, said shorter film layer and foam layer having a lobe-like formation at the bottom thereof of smaller size than the extension tab on the longer plastic layer so as to leave a part of the extension tab exposed for grasping while still forming an area which may be overlapped by the thumb adjacent to the finger on which the cot is applied.

Register, U.S. Pat. No. 3,934,299 describes a device adapted to be worn on the finger for cleaning the teeth, wherein the device has an outer surface provided with a fabric texture with the fabric being impregnated with a dentifrice material. The device has a tab at the open end thereof for facilitating the placement of the device on a finger.

Berg, U.S. Pat. No. 4,875,247 describes a disposable tooth cleaning and polishing product for manually cleaning teeth comprising a sheet of thin, flexible material such as paper, cloth or synthetic foam material which may also be formed and contoured. The material is substantially insoluble in water and oral cavity juices and has at least one surface with sufficient surface texture to remove plaque, food residue and film, and oral cavity acids from teeth surfaces by manually rubbing the material with finger pressure against the teeth while also being sufficiently soft and pliable so as to avoid injuring or abrading the gums. The formed, flexible material may have various embodiments each adapted to fit over the end of the user's finger for enhanced retention for rubbing against the teeth. The flexible sheet may also include releasable adhesion means on one surface for attachment to the fingertip and may also be retained in place against the fingertip by a ring over the finger and sheet fitted to the finger's first knuckle. A flexible sheet may be provided individually, packaged for dispensing, or in roll form perforated for convenient separation.

Hansen et al., U.S. Pat. No. 5,487,201 describes an oral wipe comprising a sleeve, the sleeve being comprised of interwoven material, the sleeve having a closed end extending to at least one corner at the closed end, a pick element comprised of a heat sealable component, and a piece of dental floss, the piece of floss having one floss end embedded and retainingly secured in the heat sealable component.

Mittiga, WO95/31154 describes a glove of fine natural or synthetic rubber for one finger of the hand having one or more operational areas prepared on the surface in a longitudinal direction to correspond especially with the position of the finger tip, to enable the teeth, gums and other parts of the oral cavity to be rubbed and massaged also with the aid of various products for cleaning the teeth such as dentifrice or others for health-giving treatment, massage and beneficial action generally.

The prior art teaches the use of oral wipes for the teeth but does not teach the present combination which provides an improved material, size and package.

SUMMARY OF THE INVENTION

The present invention teaches certain benefits in construction and use which give rise to the objectives described below.

The present invention is a dental wiper providing a package having a front panel, a rear panel and a circumferential side panel joining the front and rear panels as an integral unit defining an interior space. The front panel provides an open slot extending substantially across the package. The open slot has a central access portion with clearance for finger tip entry into the interior space of the package. A plurality of dental sheets are arranged in a stack within the package. The dental sheets each have a width approximately equal to the slot width where the dental sheets position one edge of the sheets, adjacent to the access portion of the slot for being manually engaged for withdrawal. The sheets are made of a dental floss material and are useful for manually cleaning the surfaces of the teeth.

A primary objective of the present invention is to provide an apparatus and method of use of such apparatus that provides advantages not taught by the prior art.

Another objective is to provide such an invention capable of being carried in pocket or purse for convenient use.

A further objective is to provide such an invention capable of providing an improved surface wipe for cleaning the teeth.

A still further objective is to provide such an invention capable of easy storage of surface wipes and convenient dispensing of the wipes one after the other as needed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1 is a plan view of the preferred embodiment of a wipe of the invention;

FIG. 2 is a is a perspective view of a package of the preferred embodiment with at least one of the wipes contained within;

FIG. 3 is a side view of the wipe of FIG. 1;

FIG. 4 is perspective view thereof showing a folding of the wipe of FIG. 1;

FIG. 5 is a section view taken along line 5—5 in FIG. 2; and

FIG. 6 is a perspective view of the invention showing the method of dispensing a wipe from the package.

DETAILED DESCRIPTION OF THE INVENTION

The above described drawing figures illustrate the invention in at least one of its preferred embodiments, which is further defined in detail in the following description.

The present invention is a dental wiper apparatus which comprising a package 10 preferably made of paperboard or plastic sheet stock folded into a container, and having a front panel 12, a rear panel 14 and a circumferential side panel 16 which joins the front 12 and rear 14 panels as an integral unit. The package 10 has, defined by the panels, an interior space 18. The front panel 12 provides an open slot 20 having a slot width 22 extending substantially across the front panel 12. The open slot 20 encompasses a central access portion 24 providing clearance for finger tip entry into the interior space 18 of the package 10. A plurality of dental sheets 30 are arranged or set as a stack, as shown in FIG. 5. Each one of the dental sheets 30 has a width 32 just slightly greater than the slot width 22 for improved retention of the dental sheets 30 while allowing them to be dispensed. This is considered to be a novel feature of the present invention. The dental sheets 30 are folded and placed within the package 10 so as to position one edge 34 of each of the dental sheets 30, in turn, as they are withdrawn from the package 10, in adjacency to the access portion 24 of the slot 20 in position for being manually engaged for withdrawal from the package 10 through the slot 20 as shown in FIGS. 2 and 6. The proximity of the edge of the dental sheets to the slot 20 is considered to be a novel feature of the present invention.

Advantageously, the dental sheets 30 are made up of compressed dental floss, such as a waxed cotton filament or a Teflon® micro-line, as this has been found to be readily available, easily compressed into sheet form and advantageous for the specific dental surface wiping and surface cleaning taught herein. The sheets 30 are approximately 2 by 4 inches in size, and rectangular in shape, as shown in FIG. 1. This approximates the size of an adult human palm as has been found to be novel in maintaining cleanliness of the sheets in use, i.e., providing no excess overhanging portions outside of the palm area which might result in contact with facial hair and other relatively unclean portions around the mouth; and of sufficient size for the average adult mouth, i.e., total tooth surface wiping area. Also, this size and shape has been found to be novel for its folding and dispensing characteristics, in inexpensive manufacture and convenience in carrying. Advantageously, the dental sheets are each folded, as shown in FIG. 4, such that a top edge of the sheet is adjacent to a bottom edge of the sheet. The top, preferably the above defined "one edge 34," and bottom 36 edges are positioned roughly at or near the center of the folded sheet 30, by folding as shown in FIG. 4.

The pressing of dental floss material into a sheet form is considered the central novelty of the present invention. It has been discovered that the surface of such a wiper constructed from dental floss is greatly superior to other possible material surfaces. Materials such as tissues, papers, lens cloth and other possible inexpensive materials are very much inferior in accomplishing the primary objective of the present invention, i.e., to clean the surface of the teeth from foreign matter and from surface films. It is believed that this superior result occurs due to the size and shape of the dental floss filaments as they sit on the surface of the compress sheet and as they come into contact with the tooth surface. Also, it has been found that the surfaces of the sheets 30 are not absorbent but are able to pick up moisture as from films that coat the teeth. Thus, the sheets 30 do not soften when wetted, do not degrade during use and yet are able to pick up small particles which adhere to the surfaces of the sheets 30 within the valleys formed therein. No other material has been shown to accomplish this task at an equal or near equal level. Thus the sheets 30 are a very novel commodity.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A dental wiping apparatus which comprises: a combination package having a front panel, a rear panel and a circumferential side panel joining the front and rear panels as an integral unit defining an interior space therewithin; the front panel providing an open slot having a slot width for extending substantially thereacross, the open slot encompassing a central access portion providing clearance for finger tip entry into the interior space of the package; and a plurality of dental sheets formed by compressing dental floss filament and then set as a stack, each one of the dental sheets having a width slightly larger than the slot width.

2. The apparatus of claim 1 wherein the dental sheets are folded and placed within the package so as to position at least one edge of each of the dental sheets, in turn, adjacent to the access portion of the slot in a position for being manually engaged for withdrawal, in sequence, through the slot.

3. The apparatus of claim 1 wherein the dental sheets are approximately 2 by 4 inches in size for approximating the size of, and being held within an adult human palm.

4. The apparatus of claim 1 wherein the dental sheets are each folded such that a top edge of the sheet is adjacent to a bottom edge of the sheet.

5. The apparatus of claim 4 wherein the top and bottom edges are positioned medially on the folded sheet.

* * * * *